(12) United States Patent
Knox et al.

(10) Patent No.: US 8,617,147 B2
(45) Date of Patent: *Dec. 31, 2013

(54) METHOD FOR MODIFYING THE REFRACTIVE INDEX OF OCULAR TISSUES

(75) Inventors: Wayne H. Knox, Pittsford, NY (US); Krystel R. Huxlin, Rush, NY (US)

(73) Assignee: University of Rochester, Rochester, NY (US)

( * ) Notice: Subject to any disclaimer, the term of this patent is extended or adjusted under 35 U.S.C. 154(b) by 308 days.

This patent is subject to a terminal disclaimer.

(21) Appl. No.: 12/895,978

(22) Filed: Oct. 1, 2010

(65) Prior Publication Data

US 2011/0071509 A1 Mar. 24, 2011

Related U.S. Application Data

(63) Continuation-in-part of application No. 12/146,976, filed on Jun. 26, 2008, now Pat. No. 8,486,055.

(60) Provisional application No. 60/929,397, filed on Jun. 26, 2007, provisional application No. 61/026,890, filed on Feb. 7, 2008.

(51) Int. Cl.
*A61B 18/18* (2006.01)

(52) U.S. Cl.
USPC .................................. 606/5; 606/4; 607/89

(58) Field of Classification Search
None
See application file for complete search history.

(56) References Cited

U.S. PATENT DOCUMENTS

| | | | | |
|---|---|---|---|---|
| 6,478,792 | B1 * | 11/2002 | Hansel | 606/5 |
| 2004/0243112 | A1 * | 12/2004 | Bendett et al. | 606/5 |
| 2007/0055221 | A1 * | 3/2007 | Lubatschowski et al. | 606/5 |
| 2008/0001320 | A1 * | 1/2008 | Knox et al. | 264/1.37 |
| 2009/0005764 | A1 * | 1/2009 | Knox et al. | 606/5 |
| 2009/0143858 | A1 * | 6/2009 | Knox et al. | 623/6.56 |

* cited by examiner

*Primary Examiner* — Bill Thomson
*Assistant Examiner* — Lynsey Crandall
(74) *Attorney, Agent, or Firm* — William Greener; Bond, Schoeneck & King, PLLC

(57) ABSTRACT

A method for providing vision correction to a patient. The method includes: (a) measuring the degree of vision correction needed by the patient and determining the location and shape of refractive structures that need to be positioned within the cornea to partially correct a patient's vision; (b) directing and focusing femtosecond laser pulses in the blue spectral region within the cornea at an intensity high enough to change the refractive index of the cornea within a focal region, but not high enough to damage the cornea or to affect cornea tissue outside of the focal region; and (c) scanning the laser pulses across a volume of the cornea or the lens to provide the focal region with refractive structures in the cornea or the lens. Again, the refractive structures are characterized by a change in refractive index, and exhibit little or no scattering loss.

18 Claims, 13 Drawing Sheets

METHOD FOR MODIFYING THE REFRACTIVE INDEX OF OCULAR TISSUES

REFERENCE TO RELATED APPLICATIONS

This continuation-in-part application claims the benefit under 35 U.S.C. §120 of U.S. patent application Ser. No. 12/146,976, filed Jun. 26, 2008, which is turn claims the benefit of 35 U.S.C. §119(e) to U.S. provisional application Ser. No. 60/929,397 filed Jun. 26, 2007, and U.S. provisional application Ser. No. 61/026,890 filed Feb. 7, 2008, whose disclosures are hereby incorporated by reference in their entireties into the present disclosure.

STATEMENT OF GOVERNMENT INTEREST

The U.S. Government has a paid-up license in this invention and the right in limited circumstances to require the patent owner to license others on reasonable terms as provided for by the terms of Contract No. R01 EY015836 and Grant No. 08P0EY01319F awarded by the National Institutes of Health. The government has certain rights in the invention.

FIELD OF THE INVENTION

The present invention relates to a method of using a laser to modify the refractive index of ocular tissues, e.g., the corneal stroma or lens cortex, for vision correction.

BACKGROUND OF THE INVENTION

Conventional ultraviolet nanosecond excimer lasers have been very successfully used for corneal refractive surgery such as photorefractive keratectomy (PRK), laser-assisted in situ keratomileusis (LASIK) and laser sub-epithelial keratomileusis (LASEK). By ablating corneal tissue through direct, one-photon absorption of ultraviolet light, these lasers are able to alter the curvature and thickness of corneas, ultimately altering their optical power.

The rapid development of femtosecond laser technology has provided an additional tool for corneal refractive surgery. In contrast to the photo-ablative ultraviolet lasers, femtosecond laser pulses in the near infrared or visible range can pass through transparent corneal tissue without significant one-photon absorption. Only when pulses are focused inside the cornea, is the intensity of the beam sufficient to cause non-linear, typically, multi-photon absorption. Because the absorption is nonlinear, the laser-affected region tends to be highly localized, leaving the surrounding region unaffected, or minimally affected. See, Vogel A, Noack J, Huttman G, Paltauf G, Mechanisms of femtosecond laser nanosurgery of cells and tissues. *Applied Physics B* 2005, 81, 1015-47; Loesel F H, Niemz M H, Bille J F, Juhasz T, Laser-induced optical breakdown on hard and soft tissue and its dependence on the pulse duration: experiment and model. *IEEE Journal of Quantum Electronics* 1996, 32, 1717-22; and Giguere D, Olivie G, Vidal F, et al., Laser ablation threshold dependence on pulse duration for fused silica and corneal tissues: experiments and modeling, *Journal of the Optical Society of America A* 2007, 24, 1562-68. Also, several studies on the effects of high-repetition-rate femtosecond lasers on fused silica and borosilicate glass have found that laser pulses greatly increased the temperature of the materials at the laser focus. See, Eaton et al, *Optics Express* 2005, 13, 4708-16. Vogel calculated the temperature change in water would be >10° K. with a 0.6 NA focusing lens and 100 fs laser pulses assuming that with each pulse, an energy density of 1 J/cm$^3$ at the center of the initial temperature distribution is deposited.

In the past two decades, extensive experimental and theoretical work has been done to characterize laser-induced optical breakdown thresholds in different materials, including the cornea and the lens. Most of this work, however, centered on the use of continuous wave (CW) lasers or on single pulses from low repetition rate lasers in which thermal diffusion time is much shorter than the time interval between adjacent pulses. Thus, each pulse is responsible for a change in the material. Indeed, it has been established that for pulses longer than 10 ps, the optical breakdown threshold fluence scales as the square root of the pulse duration. To date, most femtosecond lasers used to cut corneas in clinical practice use micro-Joule (µJ) femtosecond laser pulses with a low-repetition-rate (Hz-kHz range) and spot diameters of more than 5 microns (µm). See, Kurtz R M, Horvath C, Liu H H, Krueger R R, Juhasz T, Lamellar refractive surgery with scanned intrastromal picosecond and femtosecond laser pulses in animal eyes, *Journal of Refractive Surgery* 1998, 14, 541-48; and Juhasz T, Loesel C, Horvath C, Kurtz R M, Mourou G, Corneal refractive surgery with femtosecond lasers, *IEEE Journal of Quantum Electronics* 1999, 5, 902-09.

This contrasts with the range of femtosecond laser parameters that have been established for biomedical applications. See, Loesel F H, Niemz M H, Bille J F, Juhasz T, Laser-induced optical breakdown on hard and soft tissue and its dependence on the pulse duration: experiment and model, *IEEE Journal of Quantum Electronics* 1996, 32, 1717-22. Compared with the low-repetition-rate femtosecond lasers with µJ or milliJoule (mJ) pulse energies, high-repetition-rate (>1 MHz) femtosecond laser oscillators usually have pulse energies on the order of nanoJoule (nJ). Such low-pulse-energy femtosecond lasers have been used for both micromachining and nanosurgery. See, König K, Krauss O, Riemann I, Intratissue surgery with 80 MHz nanojoule femtosecond laser pulses in the near infrared, *Optics Express* 2002, 10, 171-76.

U.S. patent No. to Hansel generically describes a method and a device for irradiation of ocular tissues that can be used for such applications as refractive surgery and laser medicine. The method described is said to combine the "working principles of specific optical and electronic modules to expose the eye lens to controlled therapeutic radiation in the long-wave UV-A range above cornea absorption and/or the visible and/or the near infra-red ranges and/or the cornea in a defined way to treatment radiation in the near infra-red wavelength range about 1.3 micrometers" (see, Hansel Abstract). The therapeutic radiation is also said to provide "locally photo-induced irreversible chemical changes are created in the eye lens substance and/or the cornea substance such that the refractive index and/or the transmission properties for visible useful radiation can be changed to pre-defined parameters, resulting in a defect-reduced vision." Id.

While most femtosecond laser surgical procedures involve (by definition) some sort of disruption, either affecting membranes, organelles or other cellular components, they can be performed with such precision and selectivity so as not to kill the cells. Recently, research within our group on both silicone and non-silicone-based hydrogels, demonstrates that femtosecond micromachining works by inducing a significant change in refractive index of the materials without visible plasma luminescence or bubble formation, and without the generation of undesirable scattering or absorbing centers. See, U.S. patent application Ser. Nos. 11/745,746, filed May 8, 2007, and 11/948,298 filed Nov. 30, 2007. Our success with creating refractive structures in hydrogel materials led us to explore whether similar type structures could be created in ocular tissues.

There exists an ongoing need for ways to improve or correct vision. Changing the refractive index of ocular tissues, e.g., the corneal stroma or lens cortex, using a femtosecond laser, without tissue destruction or wound healing response would represent a major advance in the field of laser refractive correction or vision correction generally.

SUMMARY

An embodiment of the invention is directed to a method for forming a refractive structure in a living eye. The method includes the steps of directing and focusing a plurality of femtosecond laser pulses in a spectral region between about 350 nanometers (nm) to about 600 nm within a cornea or a lens of the living eye; controlling the intensity of the laser pulses to have an intensity sufficient to change the refractive index of the cornea or lens within a defined focal region, but below a damage threshold the cornea or lens, or at a level that will not photo-disrupt cornea or lens tissue outside of the focal region; and forming a refractive structure in the focal region of the cornea or the lens by scanning the laser pulses through a volume of the cornea or the lens. Each refractive structure is characterized by a change in refractive index, and exhibits little or no scattering loss.

An embodiment of the invention is directed to a method for providing vision correction to a patient. The method includes: (a) measuring the degree of vision correction needed by the patient and determining the location and shape of a refractive structure that needs to be positioned within the cornea to partially correct a patient's vision; (b) directing and focusing femtosecond laser pulses in the blue spectral region within the cornea at an intensity high enough to change the refractive index of the cornea within a focal region, but not high enough to damage the cornea or to affect cornea tissue outside of the focal region; and (c) scanning the laser pulses across a volume of the cornea or the lens to provide the focal region with a refractive structure in the cornea or the lens. Again, the refractive structure is characterized by a change in refractive index, and exhibits little or no scattering loss.

An embodiment of the invention is directed to a method for forming a refractive structure in a living eye, comprising: directing and focusing a plurality of femtosecond laser pulses in a spectral region between about 350 nanometers (nm) to about 600 nm within a defined focal region in the cornea or lens of the living eye, wherein the laser pulses have a repetition rate from 10 MHz to 300 MHz, a pulse duration of 30 fs to 200 fs, an average power from 20 mW to 160 mW, and a pulse energy from 0.01 nJ to 10 nJ; further wherein the defined focal region is in the form of a cylindrical volume having a diameter between about 1.0 µm to 2 µm and a length between about 3 µm to 6 µm; and forming a refractive structure in the focal region of the cornea or the lens, further comprising creating a difference in the refractive index of the refractive structure from that outside of the focal region by between about 0.005 to 0.06 without photo-disrupting cornea or lens tissue outside of the focal region. According to an aspect, the spectral region is between about 375 nm to about 425 nm. According to an aspect, the spectral region is between about 350 nm to about 400 nm. According to an aspect, the laser pulses have a wavelength of about 400 nm. According to an aspect, the pulse energy is between about 0.1 nJ to 2 nJ. According to an aspect, the method further comprises forming the refractive structure having a structural form of at least one of a lens, a prism, a Bragg grating, a microlens arrays, a zone plate, a Fresnel lenses, and a combination thereof.

BRIEF DESCRIPTION OF THE DRAWINGS

The embodied invention will be better understood from the following description and in consideration with the accompanying figures. It is to be expressly understood, however, that each of the figures is provided to further illustrate and describe the invention and is not intended to further limit the invention claimed.

FIGS. 13A-13C are schematic diagrams of a device in which the preferred or another embodiment can be implemented.

DETAILED DESCRIPTION OF EMBODIMENTS THE INVENTION

Figure 1:
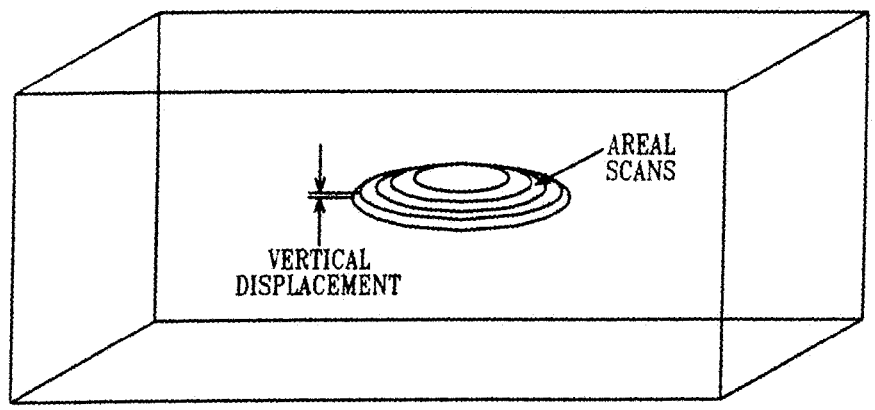
FIG. 1 is a schematic representation of a three-dimensional structure in the cornea stroma that can be produced by the method described.

Using very high-repetition-rate, ultra-short laser pulses we determined that the optical breakdown threshold for a 0.70 NA focusing condition in lightly-fixed cornea stroma and lens cortex is from about 40 mW to 90 mW average laser power, respectively. For both cornea stroma and lens cortex both values are lower than the optical breakdown power reported by König and colleagues using 1 nJ pulse energy, 170 fs pulse duration and 1.30 NA focusing in porcine corneas. See, König et al, Optics Express 2002, 10(3), 171-76. By using 30 mW and 45 mW average laser power (0.3 nJ and 0.5 nJ pulses), we discovered that one can induce Intra-tissue Refractive Index Shaping (IRIS), without accompanying photo-disruption and tissue destruction.

We adapted our femtosecond micromachining approach with hydrogel materials to carry out IRIS in biological tissues. We initially measured the optical breakdown thresholds of lightly-fixed cat corneas and lenses. We then reduced femtosecond laser pulse energies below these optical breakdown thresholds to create grating patterns that are associated with a change in the refractive index of the tissue. Our investigation has led to the development of a process to modify the refractive index of ocular tissue, e.g., corneal stroma and lens cortex, without apparent tissue destruction. Accordingly, a determination of the appropriate laser parameters is important for achieving IRIS in biological tissues. Not only does the femtosecond laser fluence at the objective focus have to be below the optical breakdown threshold of the tissue, the laser fluence must be strong enough to induce nonlinear changes in the tissues. Moreover, the scan speed must be set within a specified range.

The process involves irradiating the ocular tissue with a high repetition, low-pulse-energy, femtosecond laser. If very short laser pulses having a very select energy are focused on ocular tissue, the total intensity of light leads to a change in the refractive index of the ocular tissue in the focal region. Moreover, the region of the ocular tissue just outside the focal region is minimally affected by the laser light. As a result, select volumes of ocular tissue can be modified resulting in a change in the refractive index in these tissue volumes. Moreover, the long-term stability of the observed change in refractive index suggests permanent molecular and/or structural changes to the ocular tissue An embodiment of the invention is directed to a method for forming refractive structures in a living eye. The method includes (a) directing and focusing femtosecond laser pulses in the blue spectral region within a cornea or a lens of the living eye at an intensity high enough to change the refractive index of the cornea or lens within a focal region, but not high enough to damage the cornea or lens or to affect cornea or lens tissue outside of the focal region; and (b) scanning the laser pulses across a volume of the cornea or the lens to provide the focal region with refractive structures in the cornea or the lens. The refractive structures exhibit little or no scattering loss, which means that the structures are not clearly visible under appropriate magnification without contrast enhancement.

In one embodiment, the method can further include measuring the degree of vision correction needed by a patient following cataract surgery prior to step (a), and determining the location and shape of the refractive structures that need to be positioned within the cornea to correct the patient's vision. In another embodiment, the method can further include measuring the degree of vision correction needed by a patient prior to step (a), and determining the location and shape of the refractive structures that need to be positioned within the cornea to correct the patient's vision.

In another embodiment, the determined change in refractive index induced in cornea and lens tissue using the described process is relatively small, but very significant. Based on published values for the power (39D) and native refractive index (1.376) of the cat cornea, IRIS should generate a change in corneal power ranging between 0.14D and 0.56D (assuming an index change between 0.005 and 0.02). Similarly, for the cat lens (power=53D, refractive index of the homogeneous lens=1.554), the refractive index changes induced by micromachining should theoretically alter lenticular power by between 0.5D and 0.7D. The laser process described could completely alter the approach to laser refractive surgery and to vision correction.

In addition, the preservation of tissue clarity during the treatment allows the application of IRIS for the creation of corneal fiducial markings that could be used to align eye trackers during LASIK, and for refractive corrections in a closed-loop approach, e.g. with specific benefit for the correction of higher-order aberrations, as well as for "touch-up corrections" of ocular surface defects. Various types of refractive structures can be created in biological tissues. Examples include high refractive index structures such as Bragg gratings, microlens arrays, optical zone plates, and Fresnel lenses.

As stated, the determination and selection of the laser operating parameters are particularly important in implementing IRIS. The inventors have found that various ranges of parameters are particularly useful in implementing the present invention. In treatment of the eye, the laser wavelength should be such that the tissues through which laser pulses pass are transparent to the pulses. There should also be no damage to the retina; any change should be confined to the tissue within the focal region. Also, for non-destructive alteration of ocular tissue, a $CO_2$ laser or excimer laser should not be used, since there should be no ablation or removal of the tissue.

A laser pulse frequency from 1 MHz to 10 GHz, and preferably from 10 to 300 MHz, should be used. For example, our work used a laser pulse frequency (repetition rate) of 70 MHz to 100 MHz, e.g., about 93 MHz or about 80 MHz.

Linked to the pulse frequency is a pulse duration of about 30 fs to about 200 fs. For example, a laser pulse duration of 80 fs to 120 fs.

Linked to the pulse frequency is the average laser power. A preferable average laser power is from 1 mW to 1,000 mW, e.g., from 20 mW to 160 mW, and more preferably from 60 mW to 110 mW.

The energy of each pulse should be in a range from 0.01 nJ to 10 nJ, preferably from 0.1 nJ to 2 nJ, and more preferably less than 1 nJ. For example, we have determined that a pulse energy from 0.1 nJ to 0.5 nJ, is a preferred energy range.

The laser pulse will have a peak intensity at focus of greater than $10^{13}$ W/cm$^2$. At times, it may be advantageous to provide a laser with a peak intensity at focus of greater than $10^{14}$ W/cm$^2$, or greater than $10^{15}$ W/cm$^2$.

We found that by using femtosecond laser pulses in the blue spectral region one can achieve high native nonlinear absorption so that the observed changes in index of refraction are strongly localized in three dimensions. The wavelength is chosen such that there is minimal visual sensitivity, high retinal damage threshold, and no UV photophysical one-photon damage mechanisms induced in the eye. And furthermore, the technique is performed in such a manner that there is minimal death to the live cells in the stroma, which can reduce the wound healing response from the procedure.

Linked to one or more of the above laser pulse parameters is the speed (mm/s) at which the laser pulses is scanned across a volume of the ocular tissue. Although scanning speeds as low as 0.05 mm/s can be used depending on the equipment, types of structures to be written and type of ocular tissue, greater scan speeds in a range from 0.1 mm/s to 30 mm/s are generally preferred. We have generally utilized scan speeds of 1 mm/s to 15 mm/s, e.g., 1 mm/s, 5 mm/s, 10 mm/s and 15 mm/s keeping all other laser parameters constant (wavelength 400 nm; average laser power 80 mW, pulse duration 100 fs to form refractive structures 150 μm into the corneal stroma.

The refractive structures are formed by scanning the laser pulses across a volume of ocular tissue. In theory, each short series of laser pulses is believed to form cylindrical volumes from about 0.5 μm to 3 μm in diameter and 3 μm to 10 μm in length. By scanning the laser pulses across the tissue the cylindrical volumes form continuous refractive structures in two or three dimensions. In one embodiment, the focal region can be defined by a cylindrical volume from about 1.0 μm to 2 μm in diameter and 3 μm to 6 μm in length.

The pulse energy of the focused laser used in the method will in-part depend on the type of structures to be written into the ocular tissue, the type of ocular tissue and how much of a change in refractive index is desired. The selected pulse energy will also depend upon the scan rate at which the structures are written into the ocular tissue. Typically, greater pulse energies will be needed for greater scan rates.

The pulse width must be preserved so that the pulse peak power is strong enough to exceed the nonlinear absorption threshold of the ocular tissue. However, the glass of the focusing objective(s) significantly increases the pulse width due to the positive dispersion of the glass. A compensation scheme is used to provide a corresponding negative dispersion that can compensate for the positive dispersion introduced by the focusing objective(s). Accordingly, the term "focused" in this application refers to the focusing of light from a laser within ocular tissue using a compensation scheme to correct for the positive dispersion introduced by the focusing objective(s). The compensation scheme can include an optical arrangement selected from the group consisting of at least two prisms and at least one mirror, at least two diffraction gratings, a chirped mirror, and dispersion compensating mirrors to compensate for the positive dispersion introduced by the focus objective.

In one embodiment, the compensation scheme comprises at least one prism, in many cases at least two prisms, and at least one mirror to compensate for the positive dispersion of the focusing objective. In another embodiment, the compensation scheme comprises at least two gratings to compensate for the positive dispersion of the focusing objective. Any combination of prisms, gratings and/or minors can be used for the compensation scheme in accordance with optical principles known by those of ordinary skill in the art.

As stated, the refractive structures can be defined by two- or three-dimensional structures. The two- or three-dimensional structures can comprise an array of discrete cylinders. Alternatively, the two- or three-dimensional structures can comprise a series of lines (a grating) or a combination of an array of cylinders and a series of lines. Moreover, the two- or three-dimensional structures can comprise area or volume filled structures, respectively. These area or volume filled structures are formed by continuously scanning the laser over a select plane or volume of the ocular tissue, respectively. As stated, various types of refractive structures can be created in biological tissues. Examples include high refractive index structures such as lenses, prisms, Bragg gratings, microlens arrays, optical zone plates, and Fresnel lenses.

Figure 2:
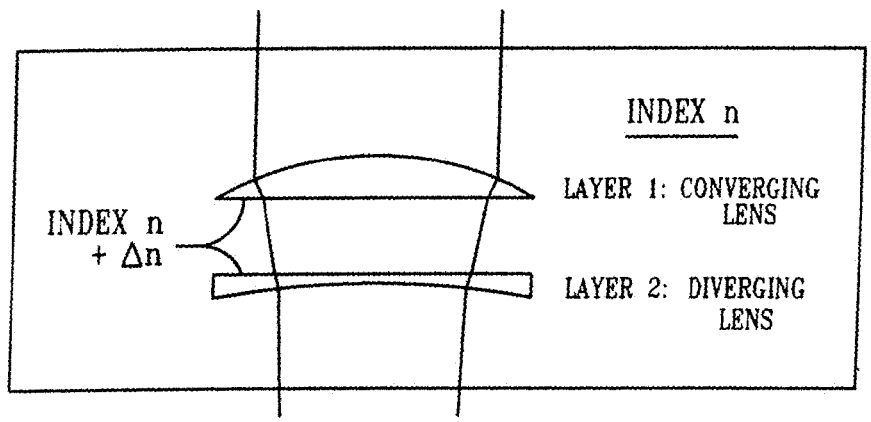
FIG. 2 is a schematic representation of creating a convex, plano or concave structure in cornea stroma to yield a positive or negative vision correction by the method described.

The area-filled or volume-filled two- or three-dimensional structures can be formed by continuously scanning the laser over select volumes of the ocular tissue. Refractive-type optical devices can be micro-machined inside the volume of ocular tissue by repeatedly scanning a tightly focused beam of femtosecond pulses in an area segment. The area of the segment can be changed correspondingly with the depth of the scan, so as to produce three-dimensionally shaped lenses with spheric, aspheric, toroidal or cylindrical shapes as shown in FIG. 1. Alternatively, refractive corrective lenses can be made in various combinations of convex, plano- or concave to yield a positive correction, or negative correction, as shown in FIG. 2. The refractive optical devices can be stacked vertically, written separately in different planes, so as to act as a single lens. Additional corrective layers can be written as desired.

In one embodiment, the focal region of the ocular tissue is defined by a series of lines in an approximately two dimensional plane having a width from 0.2 μm to 3 μm, preferably a width from 0.6 μm to 1.5 μm and a height from 0.4 μm to 8 μm, preferably a height from 1.0 μm to 4 μm (height is measured in the z direction, which is parallel to direction of the laser light). For example, one can generate a line grating comprising a plurality of lines with each line of any desired length, about 0.8 μm to about 5 μm, about 0.8 μm to about 3 μm or about 0.8 μm to about 1.5 μm in width and about 2 μm to about 10 μm about 2 μm to 5 μm in height. The lines can be separated by as little as 1.0 μm (0.5 μm spacing), and any number of lines can be incorporated into the ocular tissue. Moreover, the grating can be positioned at any selected depth (z-direction), and any number of line gratings can be generated at various depths into the ocular tissue.

In one embodiment, the refractive structures placed in corneal stroma will exhibit a change in the index of refraction of about 0.005 to about 0.06, and typically about 0.01 to about 0.04. This observed change in the index of refraction is relative to the bulk cornea stroma outside the focal region. Based on published values for the power (39D) and native refractive index (1.376) of the cat cornea, the refractive index changes induced by micromachining should generate a change in corneal power ranging between 0.1D and 01.0D or 0.1D and 0.5D (assuming that refractive index change affects the thickness of the cornea uniformly).

Our initial work with 800 nm light demonstrated that it is possible to cause low-scattering-loss, refractive index modifications in lightly-fixed cat cornea and lens using 93 MHz repetition rate, 27 fs laser pulses with 0.3 nJ and 0.5 nJ pulse energies. The use of near-infrared light that is just beyond the visual response on the long wavelength end is desirable for use in live eyes, since it would provide minimal retinal stimulation and eye aversion response. These modifications were visible only using DIC microscopy and were not associated with apparent tissue damage. The resulting modifications correspond to refractive index changes between 0.05±0.001 and 0.021±0.001. Preservation of IRIS over a month of refrigerated storage suggested that the femtosecond laser-induced modifications were likely to involve relatively long-term molecular/structural alterations. In related experiments involving silicone hydrogels, the micromachined gratings (and associated Raman spectra) are stable for at least one year, even after drying and rehydration of the hydrogel.

For example, it is possible to cause low-scattering-loss, refractive index modifications in lightly-fixed cat cornea and lens using 93 MHz repetition rate, 27 fs laser pulses with 0.3 nJ and 0.5 nJ pulse energies. These modifications were visible only using DIC microscopy and were not associated with apparent tissue damage. The resulting modifications correspond to refractive index changes between 0.05±0.001 and 0.021±0.001. Preservation of IRIS over a month of refrigerated storage suggested that the femtosecond laser-induced modifications were likely to involve relatively long-term molecular/structural alterations. In related experiments involving silicone hydrogels, the micromachined gratings (and associated Raman spectra) are stable for at least one year, even after drying and rehydration of the hydrogel.

In the spectral region around 400 nm, the human cornea starts absorbing slightly. At shorter wavelengths, this absorption becomes more significant. In a spectral window in the blue, the spectral response is minimal, yet the linear absorption is not is low enough not to cause photo-disruption of the tissue. Linear absorption in the cornea would cause unwanted attenuation of the excitation beam and unlocalized heating of the corneal tissue, which would result in cell death, which is undesirable. While the spectral region near 400 nm satisfies both requirements of minimized visual response as well as minimized linear absorption, forming of the refractive structures according to the embodied invention may be carried out between about 350 nm to about 600 nm within the defined focal region. An advantageous spectral range may be between about 375 nm to about 425 nm Another advantageous spectral range may be between about 350 nm to about 400 nm.

A Laser and Optical Configuration for Modifying Ocular Tissue

Figure 3:
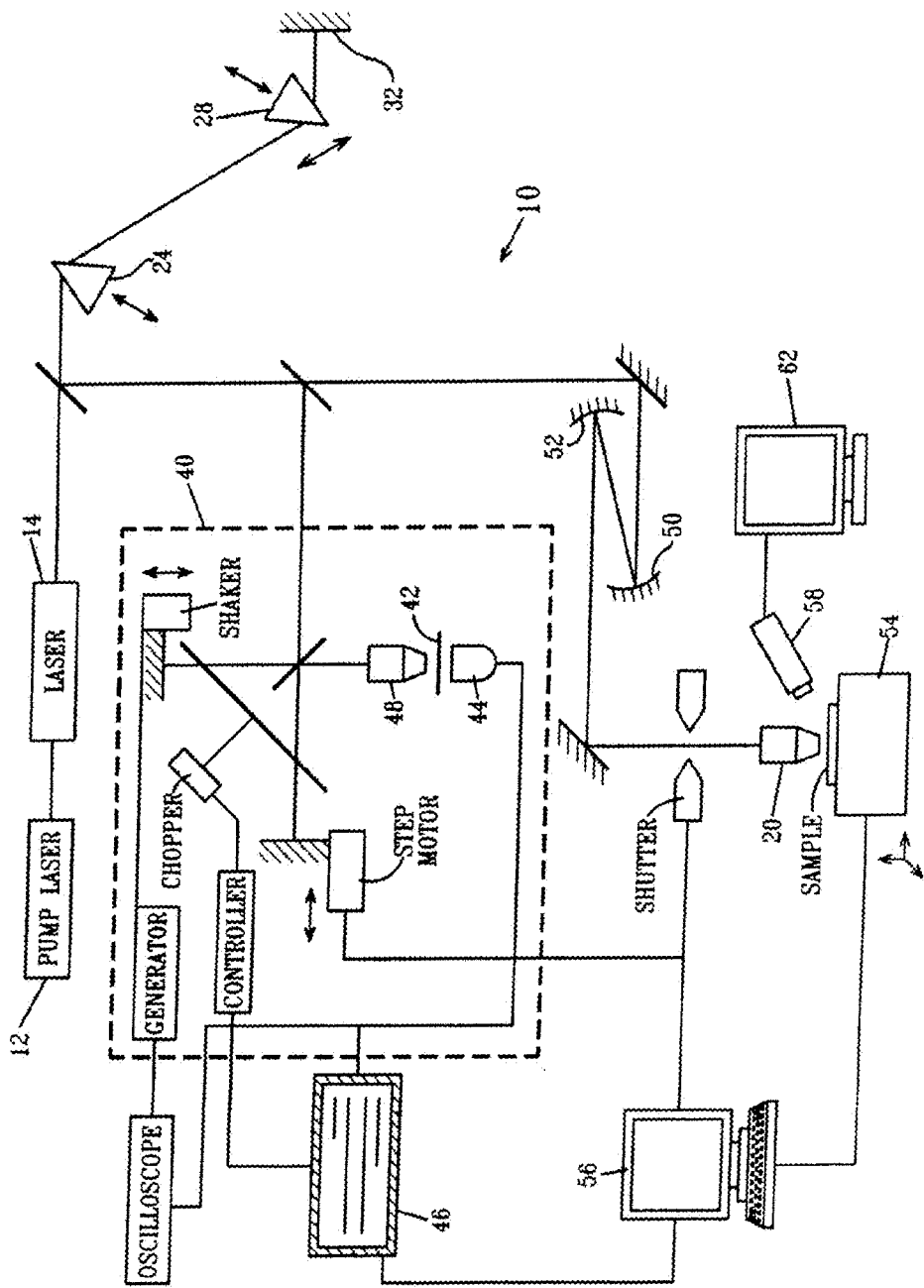
FIG. 3 is a schematic representation of the laser and optical system used to provide the refractive structures.

A non-limiting embodiment of a laser system 10 for irradiating ocular tissue with a laser to modify the refractive index of the tissue in select regions is represented in FIG. 3. A laser source comprises a Kerr-lens mode-locked Ti:Sapphire laser 12 (Kapteyn-Murnane Labs, Boulder, Colo.) pumped by 4 W of green light from a frequency-doubled Nd:YVO$_4$ laser 14. The laser generates pulses of 300 mW average power, 30 fs pulse width and 93 MHz repetition rate at wavelength of 800 nm Because there is a reflective power loss from the mirrors and prisms in the optical path, and in particular, from the power loss of the objective 20, the measured average laser power at the objective focus on the material is about 120 mW, which indicates the pulse energy for the femtosecond laser is about 1.3 nJ.

The same laser source that is used to generate 800 nm femtosecond laser pulses directly above can also be used to generate a 400 nm femtosecond (fs) laser pulse using laser optical methods and devices well known in the art. For example, we have used the Kerr-lens mode-locked Ti:Sapphire laser to generate 400 nm fs laser pulses with an average laser power of about 80 mW, and a pulse duration of about 100 fs to form refractive structures within ocular tissues, e.g., corneal stroma. As stated, the use of the shorter wavelength laser pulse verses, for example, at 800 nm, allows one to create refractive structures at much greater scan speeds for a given change in refractive index of the tissue. Also, very importantly, the shorter wavelength laser pulse allows one to make much larger changes in the refractive index of the ocular tissue that was not possible at 800 nm without approaching the damage threshold of the tissue.

Due to the limited laser pulse energy at the objective focus, the pulse width must be preserved so that the pulse peak power is strong enough to exceed the nonlinear absorption threshold of the ocular tissue. Because the glass inside the focusing objective significantly increases the pulse width due to the positive dispersion inside of the glass, an extra-cavity, compensation scheme is used to provide the negative dispersion that compensates for the positive dispersion introduced by the focusing objective. Two SF10 prisms 24 and 28 and one ending minor 32 form a two-pass one-prism-pair configuration. We used a 37.5 cm separation distance between the prisms to compensate the dispersion of the microscope objective and other optics within the optical path. A collinear autocorrelator 40 using third-order harmonic generation is used to measure the pulse width at the objective focus. Both 2nd and 3rd harmonic generation have been used in autocorrelation measurements for low NA or high NA objectives. We selected third order surface harmonic generation (THG) autocorrelation to characterize the pulse width at the focus of the high-numerical-aperture objectives because of its simplicity, high signal to noise ratio and lack of material dispersion that second harmonic generation (SHG) crystals usually introduce. The THG signal is generated at the interface of air and an ordinary cover slip 42 (Corning No. 0211 Zinc Titania glass), and measured with a photomultiplier 44 and a lock-in amplifier 46. After using a set of different high-numerical-aperture objectives and carefully adjusting the separation distance between the two prisms and the amount of glass inserted, we selected a transform-limited 27-fs duration pulse, which is focused by a 60×0.70 NA Olympus LUCPlanFLN long-working-distance objective 48.

Because the laser beam will spatially diverge after it comes out of the laser cavity, a concave minor pair 50 and 52 is added into the optical path in order to adjust the dimension of the laser beam so that the laser beam can optimally fills the objective aperture. A 3D 100 nm resolution DC servo motor stage 54 (Newport VP-25XA linear stage) and a 2D 0.7 nm resolution piezo nanopositioning stage (PI P-622.2CD piezo stage) are controlled and programmed by a computer 56 as a scanning platform to support and locate the samples. The servo stages have a DC servo-motor so they can move smoothly between adjacent steps. An optical shutter controlled by the computer with 1 ms time resolution is installed in the system to precisely control the laser exposure time. With customized computer programs, the optical shutter could be operated with the scanning stages to micro-machine different patterns in the materials with different scanning speed at different position and depth and different laser exposure time. In addition, a CCD camera 58 along with a monitor 62 is used beside the objective 20 to monitor the process in real time.

The method and optical apparatus described above can be used to modify the refractive index of ocular tissue as follows. The first step in our micromachining experiment was to establish thresholds for the optical breakdown of lightly fixed feline cornea and lens cortex. The neutral density filter was first adjusted to minimize the focused incident laser power on the cornea and the lens below their breakdown thresholds. The incident laser power was then progressively increased by adjusting the neutral density filter. The breakdown threshold power was considered to be reached when visible plasma luminescence suddenly appeared and strong scattering light as well as laser-induced damage became visible, see FIGS. 4A to 4D and FIGS. 5A and 5B. Using the 0.70 NA long-working-distance objective in our system, the measured breakdown thresholds for cat cornea and lens was about 55 mW and 75 mW average laser power, respectively, which corresponds to a pulse energy of 0.6 nJ and 0.8 nJ, respectively.

Figure 4A:
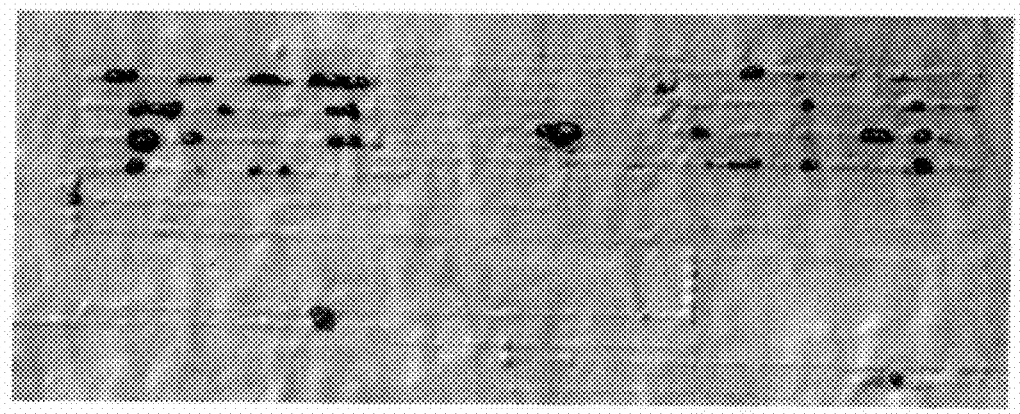
FIGS. 4A and 4C are Differential Interference Contrast (DIC) photographic images of a line grating in lightly-fixed cat corneal stroma at or near the tissue breakdown threshold.
Figure 4B:
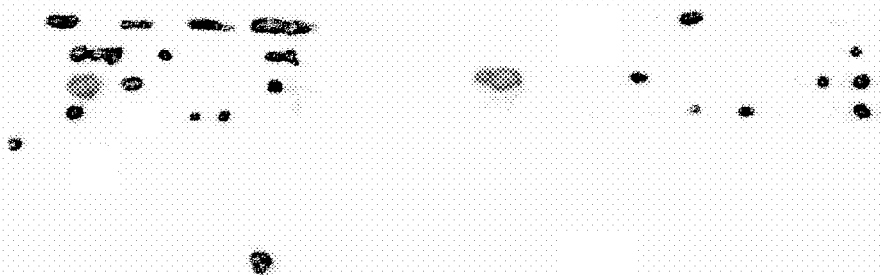
FIGS. 4B and 4D are Bright Field (BF) photographic images of a line grating in lightly-fixed cat corneal stroma at or near the tissue breakdown threshold.
Figure 4C:
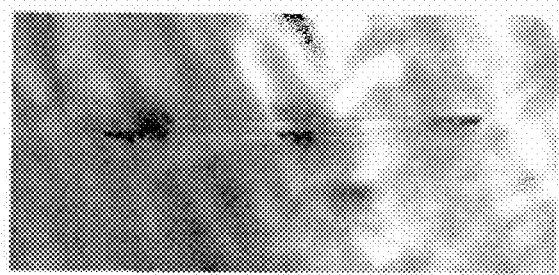
Figure 4D:
Figure 5A:
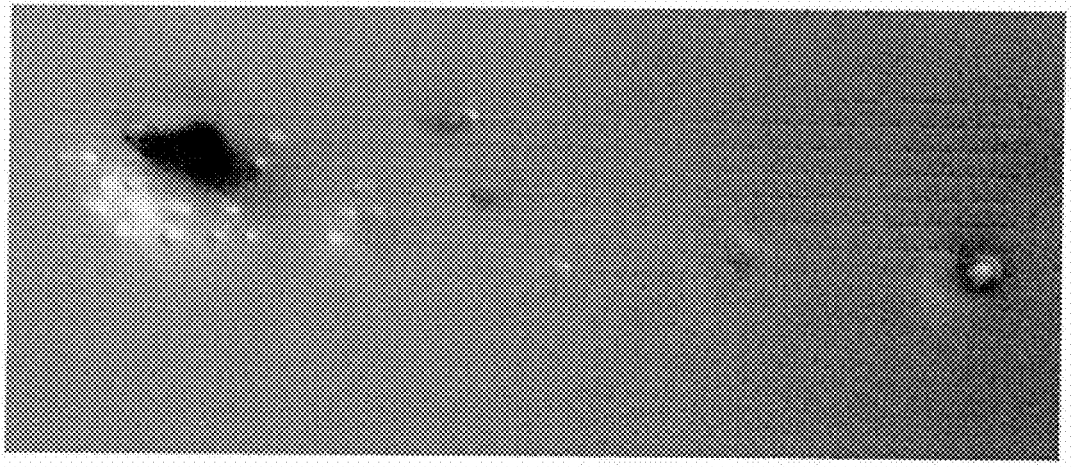
FIG. 5A is a DIC photographic image of a line grating in lightly-fixed cat lens cortex at or near the tissue breakdown threshold.
Figure 5B:
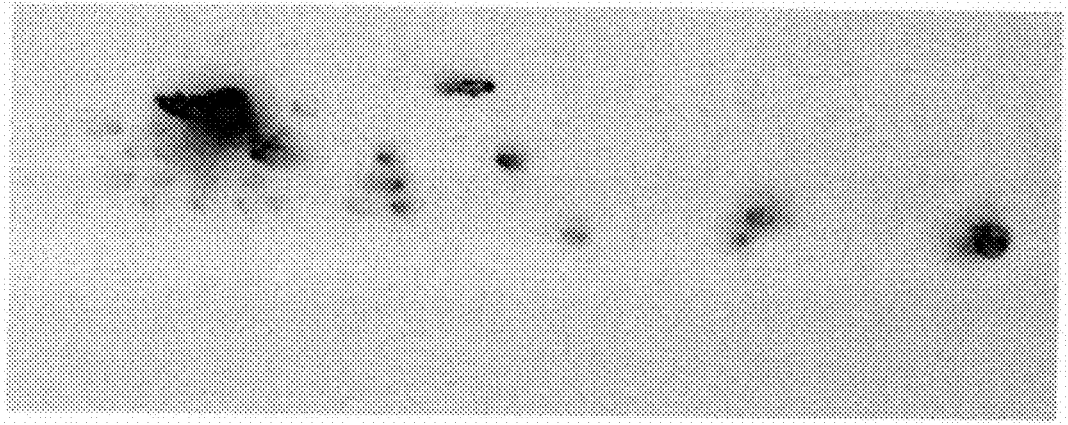
FIG. 5B is a BF photographic image of a line grating in lightly-fixed cat lens cortex at or near the tissue breakdown threshold.

FIGS. 4A to 4D are microscopic photographs of line gratings micromachined in lightly-fixed, cat corneal stroma using femtosecond laser conditions at or near the tissue breakdown threshold. FIGS. 4A and 4C are Differential Interference Contrast (DIC) images of lines created in the stroma of two different, lightly-fixed cat corneas with 0.6 nJ pulses and a scanning speed of 10 µm/s. Note, the spots of tissue destruction or "bubbles" (arrowed) along the micromachined lines (the clear, horizontal lines within stroma tissue). FIGS. 4B and 4D are Bright Field (BF) images of the same line gratings of FIGS. 4A and 4C, respectively. The BF images illustrate the visibility of tissue destruction (arrowed) and the relative invisibility of the rest of the lines that are clearly seen under DIC conditions.

Once tissue breakdown thresholds were established, the focused laser power was lowered gradually by carefully adjusting the neutral density filter until lines could be micromachined without the induction of bubbles or burns. We determined an average laser power setting of 30 mW for the cornea, which corresponds to a pulse energy of about 0.3 nJ.

The gratings were micromachined in the horizontal plane within the stroma of each corneal piece at a constant speed of 0.7 µm/s. The gratings consisted of 20-40 parallel lines, 100 µm long, 1 µm linewidth, 5 µm apart and about 100 µm beneath the corneal epithelium. Likewise, gratings were micromachined in the horizontal plane within the cortex of each lens at a constant speed of 1.0 µm/s. The gratings again consisted of 20-40 parallel lines, 100 µm long, 1 µm linewidth, 5 µm apart and about 100 µm beneath the lenticular surface. The spherical aberration at the laser focus induced by refractive index mismatch was compensated by an adjustable cover slip correction of the focusing microscope objective in order to achieve the smallest possible laser-affected region along the laser propagation direction.

Observation and Measurement of Refractive Index Change.

After writing the observed structures in both corneal stroma and lens cortex we assessed whether the micromachined gratings are associated with a change in refractive index of the two different tissues. Immediately after micromachining, the slide containing the corneal piece and lens cortex was examined under an Olympus BX51 optical microscope. Bright field, phase contrast (PC) and differential interference contrast (DIC) were used to view the gratings. The slide was then moved to another setup where a low power 632.8 nm He—Ne laser was used to irradiate the gratings. The diffraction pattern from each grating was captured by a digital camera. The refractive index changes attained were calculated as described previously. See, Ding L, Blackwell R, Künzler J F, Knox W H, Large refractive index change in silicone-based and non-silicone-based hydrogel polymers induced by femtosecond laser micro-machining, Optics Express 2006, 14, 11901-909.

In brief, the intensity of 0th order to 3rd order of diffracted light from the gratings was measured by a power meter. The different order diffraction efficiencies was obtained by calculating the ratios between the intensity of 1st, 2nd and 3rd to 0th order diffraction light. Because only one particular value of the refractive index change matches one particular diffraction efficiency value, one could calculate the index change within the femtosecond laser micromachined regions. We note that several factors could affect the results, such as the accuracy of measurement for the different diffraction order intensities, and the measurements of grating linewidth and thickness. To reduce measurement error of the diffraction order intensities, we took five measurements on each grating and calculated the average value and the standard deviation of the results. In principle, the spatial distribution of the refractive index change within the micromachined region was a small-scale gradient-index structure. For the purpose of this investigation, however, we presumed the index profile to be uniform within the grating lines, which were only 3 µm deep because the spherical aberration at the focal point was corrected.

The micromachined cat cornea and lens pieces were then removed from the glass slides after discarding the cover slips, and stored in the ethylene glycol/sucrose solution at 4° C. After one month, each corneal piece and lens piece was mounted onto a new glass slide for imaging and the diffraction light intensity measurement was repeated. This allowed us to assess whether the refractive index change initially observed had been maintained during storage.

Figure 6A:
FIG. 6A is a DIC photographic image of a line grating in lightly-fixed cat corneal stroma below the tissue breakdown threshold.
Figure 6B:
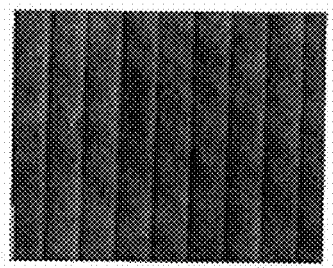
FIG. 6B is a zoomed-in DIC image of the line grating refractive structure shown in FIG. 6A.
Figure 6C:
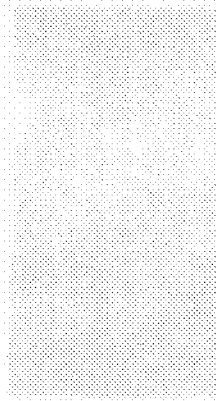
FIG. 6C is a BF photographic image of a line grating in lightly-fixed cat corneal stroma below the tissue breakdown threshold.

Exposure of lightly-fixed cat corneal to 0.3 nJ femtosecond laser pulses (30 mW average laser power) resulted in the reliable creation of grating patterns about 100 µm below the epithelial surface in all test samples, even when they were obtained from different cats. When imaged immediately after micromachining, individual grating lines could be clearly observed and distinguished with DIC microscopy (FIGS. 6A and 6B), but they were practically invisible when viewed under bright field transmission microscopy (FIG. 6C). This could be interpreted as the grating lines having very low scattering properties, which is in great contrast to the destructive tissue changes observed when laser energy was increased above the optical breakdown threshold levels (spots in FIG. 4). Using the knife-edge method, we ascertained that the laser focus diameter was 2.5 µm in air, which was much bigger than the micromachined line-widths. Therefore, it appears that only the central part of the laser focal area had sufficient intensity to modify the refractive index of corneal tissue.

Figure 7A:
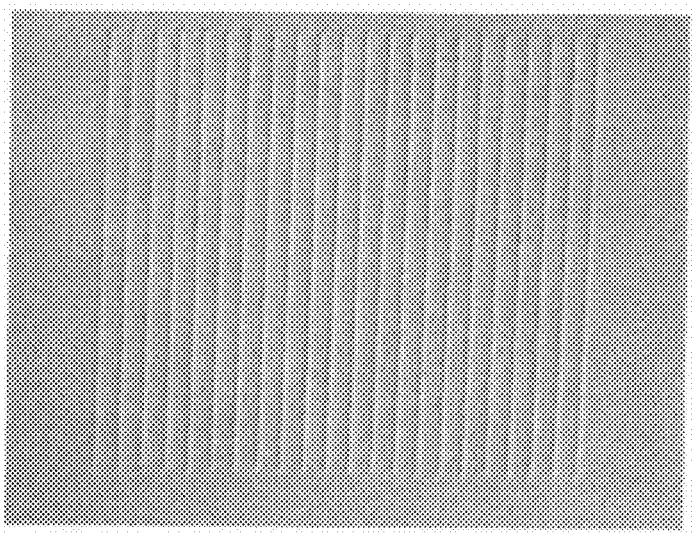
FIG. 7A is a DIC photographic image of a line grating in lightly-fixed cat lens cortex below the tissue breakdown threshold.
Figure 7B:
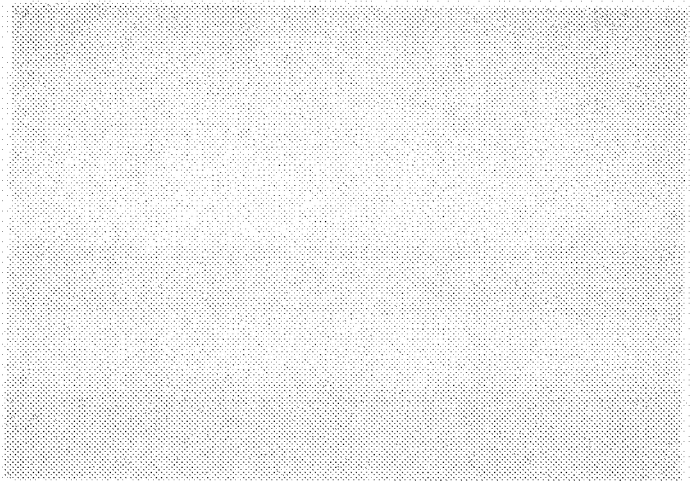
FIG. 7B is a BF photographic image of a line grating in lightly-fixed cat lens cortex below the tissue breakdown threshold.

Likewise, exposure of lightly-fixed cat lens cortex to 0.5 nJ femtosecond laser pulses (45 mW average laser power) resulted in the reliable creation of grating patterns about 100 µm below the lenticular surface in all test samples, even when they were obtained from different cats. When imaged immediately after micromachining, individual grating lines could be clearly observed and distinguished with DIC microscopy (FIG. 7A), but they were practically invisible when viewed under bright field transmission microscopy (FIG. 7B). Again, this is interpreted as the grating lines having very low scattering properties, which is in great contrast to the destructive tissue changes observed when laser energy was increased above the optical breakdown threshold levels (spots in FIG. 5). Also, it appears that only the central part of the laser focal area had sufficient intensity to modify the refractive index of lens cortex.

Figure 8A:
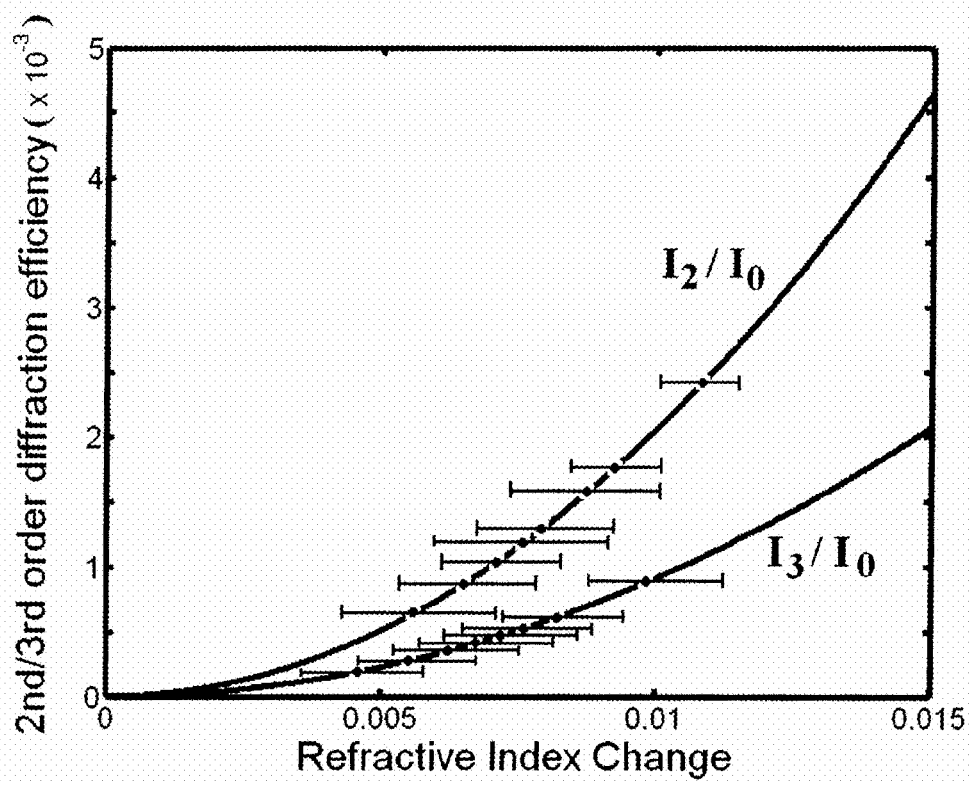
FIG. 8A is a graph plotting the 2nd and 3rd order diffraction efficiencies and the corresponding laser-induced refractive index changes of eight gratings micromachined in different corneal samples.
Figure 10A:
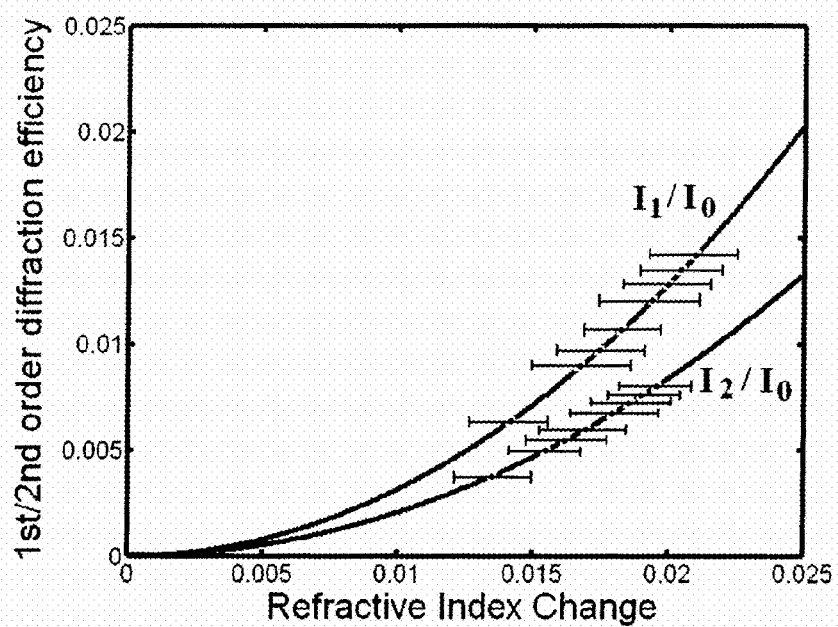
FIG. 10A is a graph plotting the 1st and 2nd order diffraction efficiencies and the corresponding laser-induced refractive index changes of eight gratings micromachined in different lens cortex samples.

In order to further assess the optical consequences of low-pulse-energy femtosecond laser micromachining on corneal stroma and lens cortex, we immediately irradiated the micromachined gratings with low power 632.8 nm He—Ne laser light. Because displacement of the stroma collagen lamellae as a result of post-mortem corneal swelling could not be completely avoided, scattering effect from the 0th order diffraction light was very strong, obscuring the 1st order diffraction light. Thus, only the 2nd and 3rd order diffraction efficiencies of each grating could be measured and used to calculate an approximate refractive index change within the femtosecond laser micromachined regions, FIG. 8A. In contrast, tissue swelling and opacification were minimal in slices of lens cortex, the 0th through 3rd order diffraction light could be measured clearly, and 1st and 2nd order diffraction efficiencies were used to calculate the induced change in refractive index (FIG. 10A).

Although a single diffraction efficiency is usually sufficient to calculate refractive index, we measured 1st/2nd or 2nd/3rd combinations to confirm that the refractive indices calculated were consistent through different diffraction orders. For these calculations, the average refractive indices of cat corneal stroma and lens were assumed to be 1.376 and 1.400, respectively. For corneal stroma, the calculated range of refractive index changes induced by the laser micromachining was from 0.005±0.001 to 0.01±0.001. For lens cortex, the calculated range of refractive index changes induced by the laser micromachining was from 0.005±0.001 to 0.03±0.001.

Figure 9A:
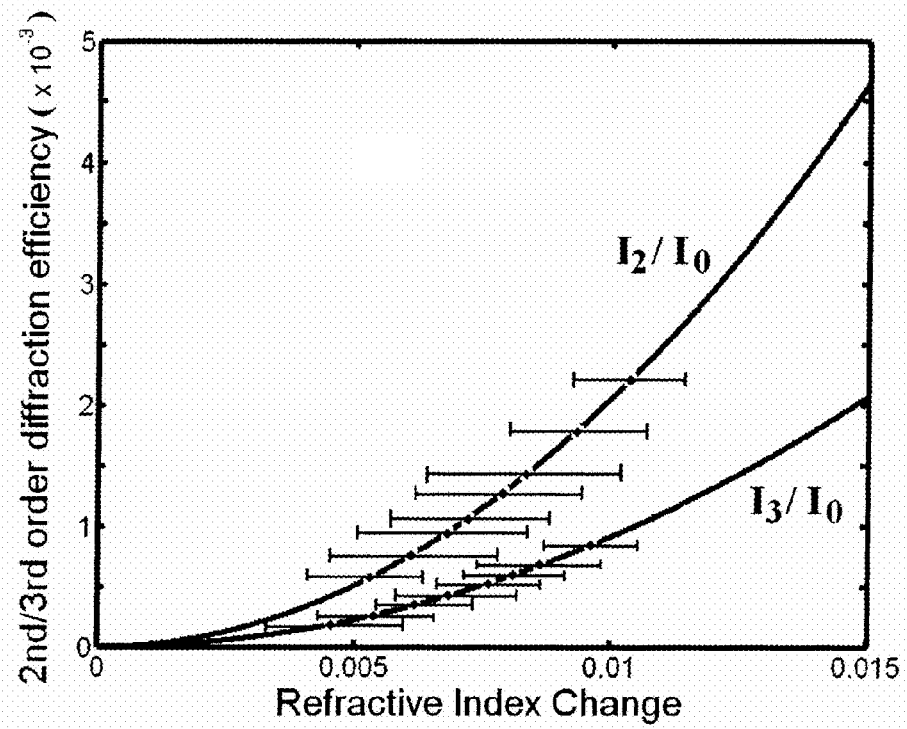
FIG. 9A is a graph plotting the 2nd and 3rd order diffraction efficiencies of eight gratings micromachined in different corneal samples after one month of storage.
Figure 9B:
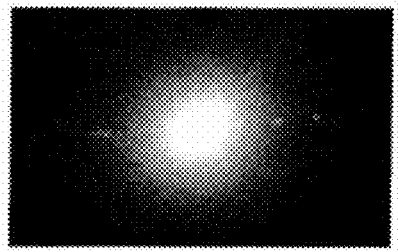
FIG. 9B is a photograph of the diffraction pattern obtained with a 632.8 nm He—Ne laser when illuminating the grating of FIG. 6A after one month.
Figure 11A:
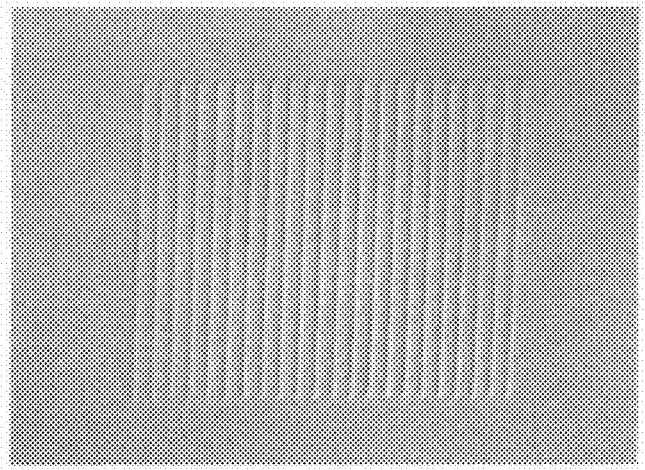
FIG. 11A is a DIC photograph showing the line grating of FIG. 7A after one month of storage.
Figure 11B:
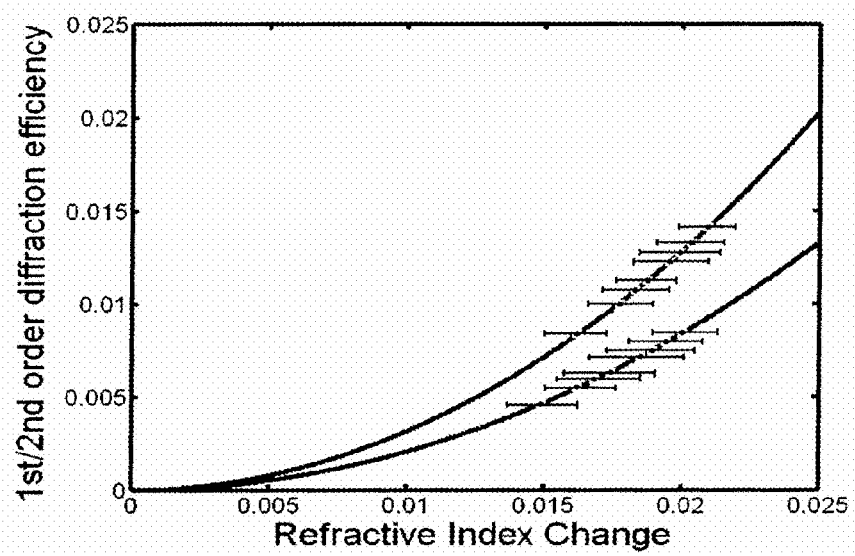
FIG. 11B is a graph plotting the 1st and 2nd order diffraction efficiencies of eight gratings micromachined in different lens cortex samples after one month of storage.

After undergoing low-pulse-energy femtosecond laser micromachining, each cornea piece was returned to the storage solution in a −20° C. freezer for one month in order to determine if the micromachined structures could be maintained over such a period of time. After one month, the cornea pieces were removed from storage and re-examined. The storage solution significantly slowed corneal swelling and opacification (relative to conventional storage in 0.1M PBS, for example), but was not able to completely prevent these events. In spite of a moderate loss of corneal transparency, DIC microscopy did reveal that the grating structures initially micromachined into the corneal stroma were still present one month after they were originally created as demonstrated by the diffraction pattern observed in FIGS. 7B and 9B. The edges of the lens slices became opaque following one month storage, but the centers remained largely transparent and the micromachined gratings were still clearly visible in a DIC image, FIG. 11A.

Figure 8B:
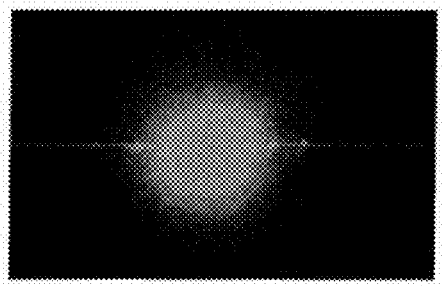
FIG. 8B is a photograph of the diffraction pattern obtained with a 632.8 nm He—Ne laser when illuminating the grating of FIG. 6A
Figure 10B:
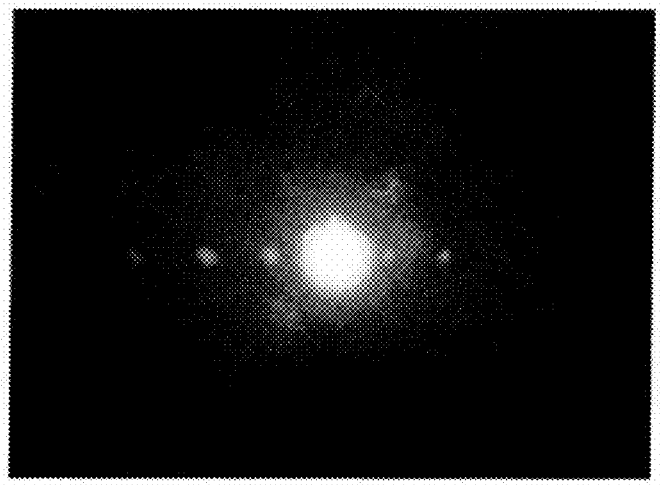
FIG. 10B is a photograph of the diffraction pattern obtained with a 632.8 nm He—Ne laser when illuminating the grating of FIG. 7A.
Figure 11C:
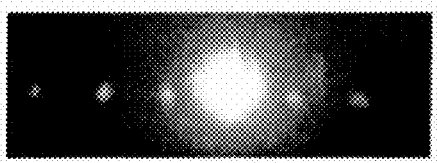
FIG. 11C is a photograph of the diffraction pattern obtained with a 632.8 nm He—Ne laser when illuminating the grating of FIG. 7A after one month.

The diffraction light distribution of one-month old gratings in corneal stroma (FIG. 9B) was again measured and found to be no different than that obtained right after the gratings' creation (FIG. 8B). Also, the diffraction light distribution of one-month old gratings in lens cortex (FIG. 11C) was again measured and found to be no different than that obtained right after the gratings' creation (FIG. 10B). In the corneal pieces, the scattering light from the 0th order diffraction still obscured the 1st order diffraction. However, the 2nd, 3rd, and even 4th order diffractions were still visible and easy to measure. In the case of the 800 nm work, the measured refractive index change after one month of storage remained from 0.005±0.001 to 0.01±0.001 for the corneal pieces and from 0.005±0.001 to 0.03±0.001 for the lens pieces.

Applications in ophthalmic surgery will now be described. As shown in FIGS. 4A to 4C, it is possible to write micronscale features into the corneal stroma with minimal scattering loss by carefully controlling the laser and scan parameters such as pulse width, average power, repetition rate, scan rate and focusing conditions. This result, which is significantly different than the results in corneal surgery that have been previously reported using femtosecond, focused pulses, suggests to us certain applications.

One such application is in writing fiducial marks in the corneal stroma. More particularly, in one application involving excimer laser ablation of the cornea for vision correction—laser in situ keratomileusis or LASIK—it is first necessary to cut across the cornea with a 'flap cutting' device. Typically, a rapidly vibrating razor blade or microkeratome is used for this purpose. This method generally produces acceptable results, however the depth of the final cut is not precise, and sometimes the degree of accommodation that can be achieved with excimer laser ablation is compromised. A competing form of corneal flap-cutting involves the use of a high-power, femtosecond laser. Femtosecond flap cutting has not been widely adopted yet in clinical refractive surgery practices, in part because of uncertainty about the long-term photochemical, mechanical and biological effects of this technique (Stonecipher et al., 2006; Wilson et al., 2007). Recently, there have been reports about negative effects of this technique, particularly in terms of tissue destruction, which appears significantly stronger than that obtained following microkeratome cutting (Stonecipher et al., 2006; Wilson et al., 2007).

Figure 12:
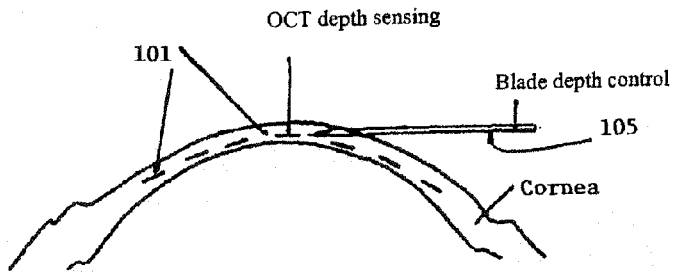
FIG. 12 is a schematic representation of a use of the preferred or another embodiment in providing fiducial marks in the cornea.

The micromachining process described provides a possible solution to the problem of being able to make a precise cut in the corneal stroma without additional tissue destruction. FIG. 12 shows a situation in which fiducial marks 101 has been machined into the stroma of the cornea, for example, at a specific location and depth. Low-energy femtosecond laser pulses can be used to write fiducial marks 101 in the stroma of the cornea at a specific depth and location. The fiducial mark 101 would not be visible to a human, as indicated by FIGS. 4b and 4D, however it is detectable by specialized optical techniques such as Optical Coherence Tomography (OCT) or Differential Interference Contrast (DIC) microscopy (FIGS. 4A and 4C).

The fiducial marks 101 could be used to 'lock' the depth of the cutting blade by using an imaging technique such as Optical Coherence Tomography (OCT). OCT has been well developed for both retinal and corneal imaging. This would ensure that the resulting depth of the blade cut would be significantly better regulated than is currently possible, even if a femtosecond laser is used to cut the corneal flap. The location and depth of a fiducial mark 101 is obtained using optical coherence tomography (OCT) interfaced with blade control, and the depth of the blade 105 is 'locked' to this depth and 'guided' along a specified cutting path, which can ensure accurate flap cutting.

Another application is in altering the optical power of the cornea. Currently, laser refractive surgery achieves changes in the optical power of the cornea by destroying/removing corneal tissue. Tissue destruction causes (1) a change in the surface profile (and curvature) of the cornea, (2) a change in corneal biomechanical properties (usually a flattening of the corneal surface), and (3) a wound healing response. A change in surface shape of the cornea as a result of points (1) and (2) is sufficient to correct large optical aberrations such as defocus and astigmatism. However, as mentioned earlier, the wound healing response that results from corneal tissue destruction limits current laser refractive procedures by decreasing their ultimate optical benefit. Exemplary femtosecond micromachining patterns that could be written into the corneal stroma include a continuous circular area, an annulus pattern, or a segmented annulus pattern.

The use of femtosecond laser pulses as described to modify the optical power of the cornea can be accomplished as follows: (1) by changing the refractive index of the cornea stroma, and (2) by altering corneal biomechanics without inducing a significant corneal wound healing response. Because of the femtosecond laser's ability to be focused non-invasively, in a non-contact manner, to effect at any chosen depth within the cornea stroma, this procedure would not require removal of the corneal epithelium or creation of a corneal flap. Epithelial manipulations are one of the major stimuli causing the wound healing response since such manipulations destroy the normally close interaction (both physically and biologically) of the corneal epithelium with its underlying stroma. The femtosecond micromachining (i.e. use of low-energy femtosecond pulses to alter tissue properties non-destructively) could be applied over a continuous area, 6-8 mm in diameter, in the center of the cornea or at particular locations in the corneal periphery as mentioned above, depending on the optical or biomechanical changes desired.

Yet another application is in altering the optical power of the intraocular lens of the eye. Presbyopia, or the loss of accommodation ability as a function of age, is currently of epidemic proportions in the developed world. The most common treatment approaches for this condition include reading glasses, bifocal glasses, contact lenses (including bifocals), multifocal laser refractive treatments, monovision laser refractive treatments and the use of accommodative intraocular lens implants into the eye. Other approaches involve the use of surgical or destructive laser treatments to punch holes in the patient's intraocular lens, thus decreasing its rigidity, and restoring some limited accommodative power. However, any invasive or destructive procedures induce a wound healing response in the lens, with increased risk of opacification or cataract formation.

The micromachining process described also provides an opportunity for an ocular surgeon to modify the refractive index of the corneal stroma layer of a patient having gone cataract surgery. The method allows the ocular surgeon to correct any aberrations as a result of the surgery. For example, starting from a lens of selected power, the power of which will vary according to the ocular requirements of the patient, the surgeon can subsequently adjust the refractive properties of the corneal stroma layer to correct a patient's vision based upon the individual needs of the patient. In essence, an intraocular lens would essentially function as a fixed power lens to correct for the refractive error of a patient's eye. The patient's vision can then be further adjusted post-implantation by modifying the refractive index of select regions of the patient's corneal stroma layer. As a result, post-operative refractive errors resulting from pre-operative measurement errors, variable lens positioning during implantation and wound healing (aberrations) can be corrected.

For instance, cataract surgery typically requires that the natural lens of each eye be replaced with an intraocular lens (IOL). Following insertion of the IOL the surgeon or eye specialist can correct for aberrations resulting from the surgery or correct for slight misplacement of the IOL. Following surgery, and after allowing time for the wound to heal, the patient would return to the surgeon to have select regions of his or her corneal stroma layer irradiated. These irradiated regions would experience a change in refractive index, which would correct for the aberrations as well as the patients needs for vision correction.

Accordingly, the invention is directed to a method comprising identifying and measuring the aberrations resulting from the surgical procedure. Once the aberrations are identified and quantified using methods well known in the art of ophthalmology, this information is processed by a computer. Of course, information related to the requisite vision correction for each patient can also be identified and determined, and this information can also be processed by a computer. There are a number of commercially available diagnostic systems that are used to measure the aberrations. For example, common wavefront sensors used today are based on the Schemer disk, the Shack Hartmann wavefront sensor, the Hartmann screen, and the Fizeau and Twymann-Green interferometers. The Shack-Hartmann wavefront measurement system is known in the art and is described in-part by U.S. Pat. Nos. 5,849,006; 6,261,220; 6,271,914 and 6,270,221. Such systems operate by illuminating a retina of the eye and measuring the reflected wavefront.

Once the aberrations are identified and quantified, the computer programs determine the position and shape of the optical structures to be written into the corneal stroma to correct for those aberrations. These computer programs are well known to those of ordinary skill in the art. The computer than communicates with the laser-optical system and select regions of corneal stroma are irradiated with a focused, visible or near-IR laser having a pulse energy from 0.01 nJ to 1.0 nJ. Alternatively, one can use 400 nm laser light with a similar pulse energy to generate even greater changes in the refractive index of corneal stroma.

The described micromachining process can also be used for custom vision correction of higher order wavefront aberration in the optical path of the eye. The basic technology for detecting and correcting aberrations of at least third-, fifth-, and tenth orders is taught in U.S. Pat. No. 5,777,719, whose disclosure is hereby incorporated by reference in its entirety into the present disclosure. Given that the region of refractive index change generated by femtosecond laser micromachining can be as small as 1 μm in diameter, this will make it possible to correct small, localized optical wavefront aberrations (higher order aberrations) in the optical path of the eye. Such aberrations exist both naturally, or can be induced by ocular surgeries, such as laser refractive surgery, corneal transplantation and wound healing following trauma to the eye.

Figure 13C:
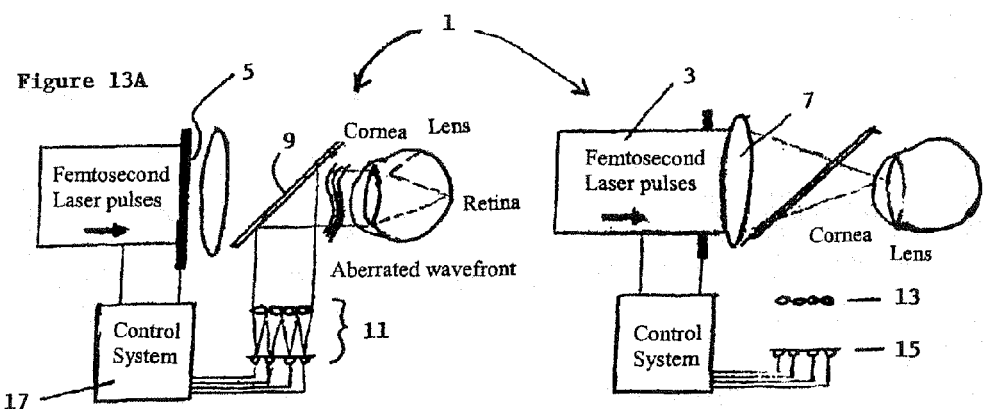
Figure 13C:
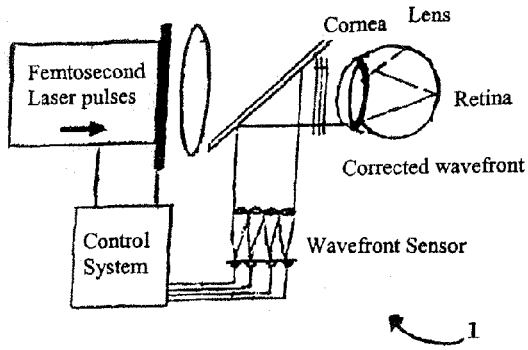

FIGS. 13A to 13C show a schematic diagram of a device 1 used to carry out the preferred embodiment or another embodiment. The device 1 includes a laser 3 for emitting femtosecond laser pulses, a shutter 5, a focusing lens 7, a dichroic mirror 9, a wavefront sensor 11 having a lenslet array 13 and a detector array 15, and a control system 17 for controlling the operations described herein.

As illustrated in FIGS. 13A to 13C, the process we propose would include the following steps: (1) using a wavefront sensor to detect and measure the lower and higher order aberrations along the optical path of a given eye, (2) calculating the topography and magnitude of refractive index changes required to achieve the necessary aberration correction, (3) focusing the femtosecond laser pulses either into the cornea or intraocular lens in order to carry out the micromachining necessary to induce the required refractive index change. Once the micromachining is complete, the wavefront sensor would be used once again to check the correction of the ocular wavefront. Since the resolution of the femtosecond laser micromachining is about 1 μm, this noninvasive method could be used as a complement or an alternative method for current customized wavefront correction methods.

In FIG. 13A, the shutter 5 is closed for detection of wavefront aberration from the optical path through the wavefront sensor 11, using aberrated light reflected from the retina of the eye. In FIG. 13B, the shutter 5 is open, and light pulses from the femtosecond laser 3 are used to correct the aberration by locally changing the index in the cornea or the lens of the eye. In FIG. 13C, after femtosecond laser 3 micromachining, the wavefront correction is verified once again using the wavefront sensor 11.

Calculation of Change in Refractive Index.

As mentioned. these gratings were investigated by focusing an unpolarized He—Ne laser beam with a wavelength of 632.8 nm on these gratings and monitoring the diffraction pattern. The diffraction angles showed good agreement with the diffraction equation $$m\lambda = d \sin \theta \quad (1)$$

where m is the diffraction order, λ is the wavelength of the incident laser beam which here is 632.8 nm, and d is the grating period.

The diffraction efficiency of the grating can be measured, and since the efficiency is a function of the refractive index change, it may be used to calculate the refractive index change in the laser irradiation region. Consider the grating as a phase grating, its transmittance function could be written as $$t(x_0, y_0) = (e^{i\phi_2} - e^{i\phi_1}) rect\left(\frac{x_0}{a}\right) * \frac{1}{d} comb\left(\frac{x_0}{d}\right) + e^{i\phi_1} \quad (2)$$

where a is the grating line width, d is the groove spacing, $\phi_2$ and $\phi_1$ are the phase delays through the lines and ambient region respectively, $$\phi_2 = 2\pi \times \frac{(n+\Delta n) \times b}{\lambda} \text{ and } \phi_1 = 2\pi \times \frac{n \times b}{\lambda},$$

b is the thickness of the grating line, n is the average refractive index of the material, Δn is the average refractive index change in the grating lines, and λ is the incident light wavelength of the measurement (632.8 nm). Here, the grating line width is 1 μm and the thickness is 3 μm. The index change within the laser effect region can be approximated to be uniform. The convolution theorem can be used to calculate the spectrum of the grating such as $$T(f_x, f_y) = F\{t(x_0, y_0)\} = (e^{i\phi_2} - e^{i\phi_1}) a \sin c(af_x) comb(df_x) \delta(f_y) + e^{i\phi_1} \delta(f_x, f_y) \quad (3)$$

Then, the intensity distribution of the grating diffraction pattern is:

$$I(x, y) = \left(\frac{1}{\lambda z}\right)^2 \times$$

$$\left[(e^{i\phi_2} - e^{i\phi_1})\frac{a}{d}\sum_{n=-\infty}^{\infty} sinc\left(\frac{an}{d}\right)\delta\left(\frac{x}{\lambda z} - \frac{n}{d}, \frac{y}{\lambda z}\right) + e^{i\phi_1}\delta\left(\frac{x}{\lambda z}, \frac{y}{\lambda z}\right)\right]^2 \quad (4)$$

From this formula, the intensity of the 0th (I0), 1st (I1), and 2nd (I2) order diffraction light is $$I_0 = \left(\frac{1}{\lambda z}\right)^2 \times \left[\left(e^{i2\pi \times \frac{(n+\Delta n) \times b}{\lambda}} - e^{i2\pi \times \frac{n \times b}{\lambda}}\right)\frac{a}{d} + e^{i2\pi \times \frac{n \times b}{\lambda}}\right]^2 \quad (5)$$

$$I_1 = \left(\frac{1}{\lambda z}\right)^2 \times \left[\left(e^{i2\pi \times \frac{(n+\Delta n) \times b}{\lambda}} - e^{i2\pi \times \frac{n \times b}{\lambda}}\right)\frac{a}{d} sinc\left(\frac{a}{d}\right)\right]^2 \quad (6)$$

and $$I_2 = \left(\frac{1}{\lambda z}\right)^2 \times \left[\left(e^{i2\pi \times \frac{(n+\Delta n) \times b}{\lambda}} - e^{i2\pi \times \frac{n \times b}{\lambda}}\right)\frac{a}{d} sinc\left(\frac{2a}{d}\right)\right]^2 \quad (7)$$

By comparing the light intensities of $1^{st}$, $2^{nd}$ and $0^{th}$ diffraction orders, the refractive index change within the grating lines can be determined.

While specific embodiments of the present invention have been described in the foregoing, it will be appreciated by those skilled in the art that many equivalents, modifications, substitutions, and variations may be made thereto without departing from the spirit and scope of the invention as defined in the appended claims.

EXAMPLES

Extraction and Preparation of Cat Corneas

Eight corneas and eight lenses were extracted under surgical anesthesia from five normal, adult domestic short-hair cats (felis cattus). All animal procedures were conducted in accordance with the guidelines of the University of Rochester Committee on Animal Research, the ARVO Statement for the Use of Animals in Ophthalmic and Vision Research, and the NIH Guide for the Care and Use of Laboratory Animals. Feline corneas and lenses were chosen because of their similarity to human corneas and lenses in terms of histological structure, molecular composition and optical properties. See, Hughes A. The topography of vision in mammals of contrasting life style: comparative optics and retinal organization. Handbook of Sensory Physiology, VII/5. Berlin: Springer Verlag; 1977. Also, in contrast with the problems associated with obtaining post-mortem human eyes, using cat corneas and lenses allowed us to precisely control post-mortem extraction time and tissue processing parameters. This was important to avoid degradation and opacification of the corneas and lenses prior to femtosecond laser micromachining. Extracted feline tissues were immediately drop-fixed for 10 minutes (corneas) in a solution consisting of 1% paraformaldehyde in 0.1M phosphate buffered saline (PBS), pH 7.4. Lenses were cut into 500 μm thick slices using a vibratome. The lens slices and whole corneas (~500 μm thick) were immersed in a mixture of 30% ethylene glycol+30% sucrose in 0.1M PBS, pH 7.4 at 4° C. The ocular tissues were stored in this solution at all times in order to minimize tissue swelling and loss of transparency.

Femtosecond Laser Micromachining

For laser micromachining, the corneas were trimmed to generate small, flat pieces of tissue, averaging ~1 cm². Each piece of cornea was then flattened onto a clear glass slide (1×3 inches, 1 mm thick, Surgipath Medical Industries Inc., IL) with the epithelium facing up and the endothelium facing down. A glass coverslip (Corning No. 0211 Zinc Titania glass) was placed on the top of each piece of cornea or lens, stabilizing it for the duration of the experiment. The ethylene glycol/sucrose storage solution was used as mounting medium to prevent or at least minimize dehydration of the cornea and lens since these effects are known to alter the refractive index and transparency of both these tissues.

Example 1

Femtosecond laser micro-machining was conducted as previously described in U.S. patent application Ser. No. 11/745,746, filed May 8, 2007 and U.S. patent application Ser. No. 11/948,298, filed Nov. 30, 2007. The laser source was a Kerr-lens mode-locked Ti:Sapphire laser (K-M Labs). This laser oscillator generates pulses averaging 300 mW, pulse duration of 27 fs and a 93 MHz repetition rate at 800 nm wavelength. A continuously variable, metallic, neutral density filter was inserted into the optical path and used to adjust the incident laser power onto each cat cornea piece. The femtosecond laser pulses were focused 100 μm below the tissue surface using a 60X, 0.70 NA Olympus LUCPlanFLN long-working-distance microscope objective. Because the large amount of glass within the microscope objective induces significant chromatic dispersion into the femtosecond laser pulses, greatly broadening the femtosecond pulse durations, we used a standard extra-cavity-prism double-pass configuration to compensate for the dispersion and maintain the ultrashort pulse duration. By carefully adjusting this dispersion compensator, we obtained nearly transform-limited 27 fs duration pulses at the focal point of the focusing objective which were measured by a collinear autocorrelator using 3rd order surface harmonic generation (THG). During femtosecond laser micromachining, the slide containing the biological tissue samples was mounted on a 3D scanning platform consisting of a Physik Instrumente (PI) P-622.2CD XY scanning stage with 250 μm travel range and 0.7 nm close-loop resolution, and a Newport VP-25XA linear servo Z-axis scanning stage with 25 mm travel range and 100 nm resolution. An infrared CCD camera was used to monitor the micromachining process and the generation of visible plasma luminescence in real-time.

Our experiments were conducted at room temperature (~25° C.). It took about 40 minutes to create a (100 μm×50 μm) grating and conduct the immediate post-micromachining measurements. Corneal trimming and mounting did not exceed 10 minutes in duration, and the corneal tissue was exposed to ambient air during the trimming process for at most 2 minutes. Application of the Ti:Sapphire femtosecond as described resulted in the formation of micromachined gratings having 20 to 40 lines into the stroma of the corneas; each line approximately 1 μm wide, 100 μm long and 5 μm apart. Refractive index changes in the micromachined regions were calculated immediately and after one month of further storage by measuring the intensity distribution of diffracted light when the gratings were irradiated by 632.8 nm wavelength He—Ne laser light. Because we observed no significant changes in cornea and lens transparency or thickness at the end of our micromachining experiments, we conclude that the described micromachining process did not cause significant corneal or lenticular dehydration or swelling.

Example 2

Irradiation of Cat Corneas at 400 Nm

Figure 14:
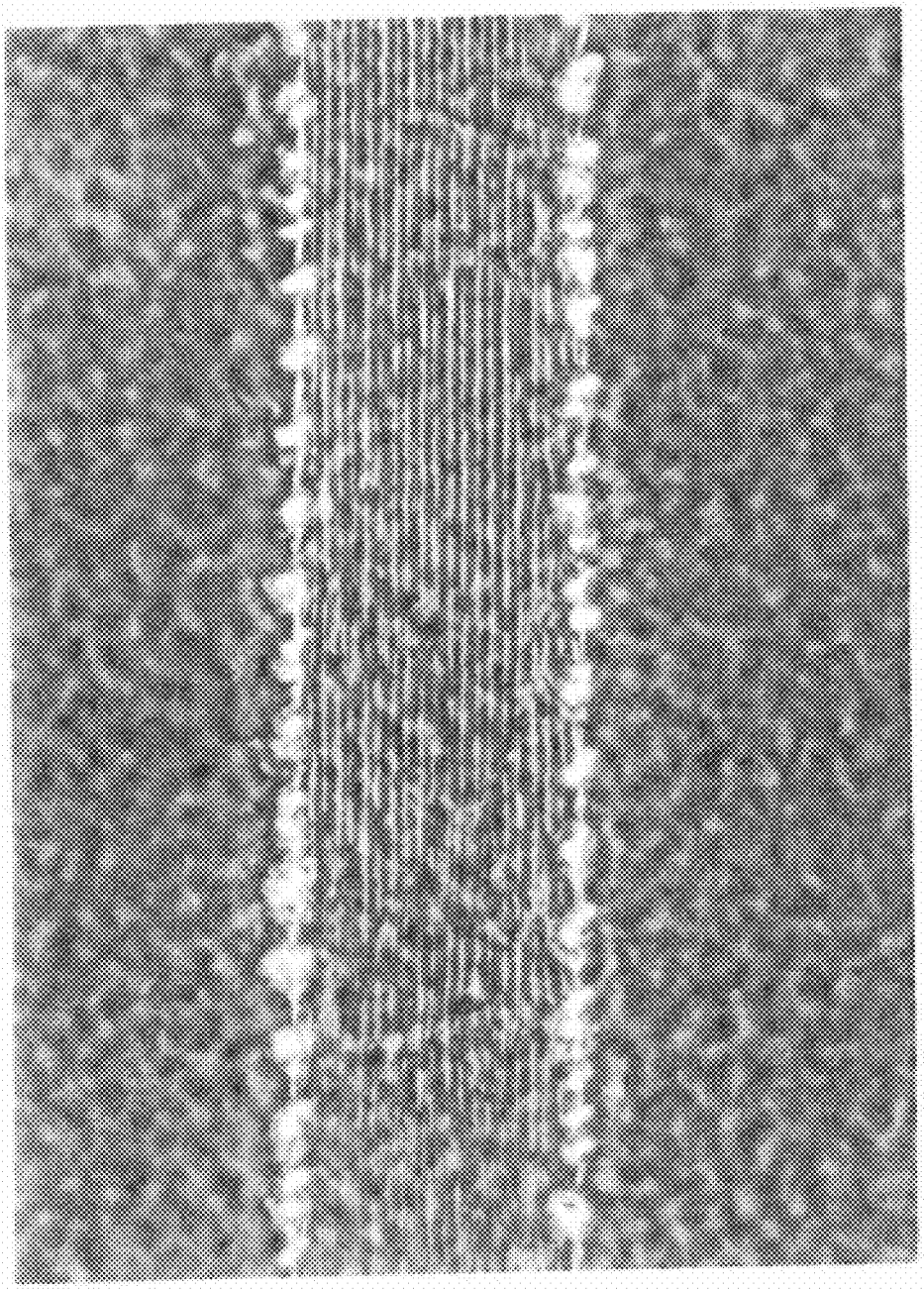
FIG. 14 is a phase contrast photographic image of a line grating in cat corneal stroma below the tissue breakdown threshold (middle line pattern) bordered by damage lines using 800 nm femtosecond laser pulses.

Using the laser system described in Example 1 but doubling the wavelength of the light to 400 nm and making slight changes in other laser operating parameters one is able to dramatically increase the process efficiency for the formation of refractive structures in cat corneas. In one embodiment, we formed a series of refractive (line) gratings with a line spacing of 5 μm about 150 μm from the top surface of the cornea with Ti:Sapphire femtosecond laser above. The average laser power was 80 mW, the pulse duration was about 100 fs and we varied the scan speed from 1 mm/s to 15 mm/s. At the slower speeds, i.e., 1 and 2 mm/s, we observed some damage to the cornea tissue, particularly at 1 mm/s scan speed. Increasing the scan speed to 5, 10 or even 15 mm/s provided refractive structures that could only be observed using a phase contract adjustment to the photomicrograph. The measured change in the refractive index of the focal regions for the 5, 10 and 15 mm/s scans were 0.037, 0.03 and 0.22, respectively. FIG. 14 is a phase contrast micrograph of a refractive structure in the form of a line grating described above that was obtained at a scan speed of 15 mm/s.

To determine the degree of physical change or potential damage (cell death) to the corneal stroma by the micromachining process described on can use In vivo confocal microscopy (IVCM), first described by Minsky. See, Minsky M., Memoir on inventing the confocal microscope. *J. Scanning* 10, 128-138 (1988). IVCM allows in vivo examination of the human cornea and conjunctiva at the cellular level. IVCM is able to demonstrate the characteristic corneal and conjunctival anatomy in vivo at the cellular level. Normal corneal innervation and cell distribution, as well as changes associated with age, contact lens wear and systemic disease such as diabetes can be documented in vivo with this technique. IVCM has been used to evaluate postsurgical procedures including refractive surgery, UV-crosslinking, keratoplasty and amniotic membrane transplantation to evaluate corneal wound healing. Several principles are realized in confocal microscopes: tandem-scanning, scanning-slit and laser-scanning confocal microscopy. Although it has high axial and transverse resolution, tandem-scanning IVCM is not able to visualize specific structures in the cornea, such as basal epithelial cells, due to its low light throughput. However, it may be superior when scanning the corneal endothelium.

Another minimally invasive technique that can be used to assess physical changes in the corneal stroma as a result of the described micromachining process is the combination of reflective confocal microscopy with multiphoton microscopy first reported by Denk et al., *Science* 1990, 73-76. See, Dong, Chen-Yuan, et al., *Microscopy Research and Technique* 2008, 71, 83-85. The two imaging modalities allow detection of complementary information from the cornea. The assessment of epithelial cellular boundaries and nuclei, the Bowman's layer and the keratocytes can be detected in the reflected confocal imaging mode, whereas the epithelial cell cytoplasm and the structural collagen can be detected in the multiphoton imaging mode.

We claim:

1. A method for forming a refractive structure in a living eye, comprising:
   (a) directing and focusing a plurality of femtosecond laser pulses in a spectral region from between 350 nanometers (nm) to 600 nm within a cornea or a lens of the living eye;
   b) controlling the intensity of the laser pulses to have an intensity sufficient to change the refractive index of the cornea or lens within a defined focal region, but below a damage threshold the cornea or lens, or at a level that will not photo-disrupt cornea or lens tissue outside of the focal region; and
   (c) forming a refractive structure in the focal region of the cornea or the lens by scanning the laser pulses through a volume of the cornea or the lens.

2. The method of claim 1, further comprising creating a difference in the refractive index of the refractive structure in the cornea or lens from that outside of the focal region by between 0.005 to 0.06.

3. The method of claim 1, further comprising forming the refractive structure having no scattering of visible light.

4. The method of claim 1, wherein the refractive structure has a structural forms of at least one of a lens, a prism, a Bragg grating, a microlens arrays, a zone plate, a Fresnel lenses, and a combination thereof.

5. The method of claim 1, further comprising measuring the degree of vision correction needed by a patient following cataract surgery prior to step (a), and determining the location and shape of the refractive structure to be formed within the cornea so as to improve or correct the patient's vision.

6. The method of claim 1, further comprising measuring the degree of vision correction needed by a patient prior to step (a), and determining the location and shape of the refractive structure to be positioned within the cornea or lens to improve or correct the patient's vision.

7. The method of claim 1, wherein the femtosecond laser pulses have a repetition rate from 10 MHz to 300 MHz, and a pulse duration of 30 fs to 200 fs.

8. The method of claim 7, wherein the femtosecond laser pulses have an average power from 20 mW to 160 mW.

9. The method of claim 7, wherein the femtosecond laser pulses have a pulse energy from 0.01 nJ to 10 nJ.

10. The method of claim 9, wherein the pulse energy is from 0.1 nJ to 2 nJ.

11. The method of claim 1, wherein the focal region is the form of cylindrical volumes from 0.5 μm to 3 μm in diameter and 3 μm to 10 μm in length.

12. The method of claim 11, wherein the defined focal region is in the form of a cylindrical volume having a diameter between 1.0 μm to 2 μm and a length between about 3 μm to 6 μm.

13. The method of claim 1, wherein directing and focusing the femtosecond laser pulses within the cornea of the living eye further comprises minimizing cell deaths in the stroma.

14. The method of claim 1, further comprising directing and focusing the plurality of femtosecond laser pulses in a spectral region from between 375 nm to 425 nm.

15. The method of claim 1, further comprising directing and focusing the plurality of femtosecond laser pulses in a spectral region from between 350 nm to 400 nm.

16. The method of claim 1, further comprising measuring a degree of vision correction needed by a patient and determining a location and a shape of refractive structures within the patient's cornea to partially correct the patient's vision.

17. The method of claim 16, further comprising directing and focusing the plurality of femtosecond laser pulses in a spectral region from between 375 nm to about 425 nm.

18. The method of claim 16, further comprising directing and focusing the plurality of femtosecond laser pulses in a spectral region from between 350 nm to 400 nm.

* * * * *